United States Patent [19]
Horrocks et al.

[11] Patent Number: 5,715,826
[45] Date of Patent: Feb. 10, 1998

[54] METHOD AND DEVICE FOR ASSESSING THE STATE OF BLOOD VESSELS

[75] Inventors: Michael Horrocks; Robert Skidmore, both of Bristol, England

[73] Assignee: British Technology Group Limited, London, England

[21] Appl. No.: 617,922

[22] PCT Filed: Sep. 14, 1994

[86] PCT No.: PCT/GB94/01997

§ 371 Date: Mar. 8, 1996

§ 102(e) Date: Mar. 8, 1996

[87] PCT Pub. No.: WO95/07651

PCT Pub. Date: Mar. 23, 1995

[30] Foreign Application Priority Data

Sep. 14, 1993 [GB] United Kingdom ............... 9318932

[51] Int. Cl.⁶ .................................................. A61B 5/02
[52] U.S. Cl. ....................................... 128/672; 128/687
[58] Field of Search ................................. 128/668, 672, 128/673, 675, 677–682, 687–690

[56] References Cited

U.S. PATENT DOCUMENTS

| | | | |
|---|---|---|---|
| 5,050,613 | 9/1991 | Newman et al. | 128/670 |
| 5,101,828 | 4/1992 | Welkowitz et al. | 128/668 |
| 5,265,011 | 11/1993 | O'Rourke | 128/672 |

FOREIGN PATENT DOCUMENTS 2 147 703  5/1985  United Kingdom.
92/22239  12/1992  WIPO.

OTHER PUBLICATIONS

Wyatt et al: "Impedance analysis to identify the at risk femorodistal graft", Journal of Vascular Surgery, vol. 13, No. 2, Feb. 1991, pp. 284–293, cited in the application, see p. 285, left column, line 14–line 46, see figure 1.

Primary Examiner—Jennifer Bahr
Assistant Examiner—Bryan K. Yarnell
Attorney, Agent, or Firm—Cushman Darby & Cushman IP Group of Pillsbury Madison & Sutro LLP

[57] ABSTRACT

A method and device for use in assessing the state of blood vessels within the human or animal body is provided. A vessel segment is identified for investigation, and at least one blood pressure responsive device is used to obtain pulse volume recordings of different sites, representing pressure at sites proximal and distal to the vessel segment. From the waveform signals obtained, Fourier transform spectra are determined for the respective sites and the transfer function between them is calculated. This is then analyzed to determine a clinically significant parameter, such as the integral of the transfer function, and this can be compared with a predetermined value to provide an indication as to the state of the vessel segment.

12 Claims, 2 Drawing Sheets

METHOD AND DEVICE FOR ASSESSING THE STATE OF BLOOD VESSELS

This application claims benefit of international application PCT/GB94/01997, filed Sep. 14, 1994.

INTRODUCTION

The present invention relates generally to vascular investigation and more specifically to a method and device for use in assessing the state of blood vessels within the human or animal body.

PRIOR ART

Vascular diseases involving sclerosis, stenoses or occlusions can be very difficult to diagnose before their effects strike. Progressive narrowing of arteries, if not identified and treated, can lead to total occlusion. Depending on the site, this may lead to the loss of a leg, or cause a heart attack or stroke. If a stenosis can be detected at an early stage, remedial measures may be taken, such as arterial reconstruction and/or angioplasty. Monitoring of haemodynamic characteristics, such as blood pressure, as an aid in indicating or assessing vascular disease, is unreliable. It is estimated that a vessel has to be occluded by more than 50% of cross sectional area before a drop in peak pressure across a stenosed segment is perceptible.

At present there are a number of methods available to physicians to aid in the detection of vascular disease. Some are invasive methods, such as that of introducing a catheter into an artery under investigation and thereby examining directly or indirectly the internal state of the vessel, be it by use of direct pressure monitoring techniques, ultrasound, camera techniques, or otherwise. Such methods are clearly not without their dangers.

There are also a number of non-invasive techniques widely used in such investigations, such as a variety of imaging techniques. Colour flow duplex ultra-sonography is one such technique, but this involves expensive equipment and requires an operator highly skilled in the interpretation of the results. Angiography is an alternative technique, in which radio-opaque contrast is introduced into the vascular system and X-ray methods are used to image the arterial lumen to enable identification and location of stenoses and occlusions. This is a relatively straightforward technique but is still highly operator-dependent in terms of the skill and experience needed to interpret the results. A 3-dimensional, or at least biplanar, approach must be taken to successfully apply the above imaging technique, as a stenosis perceptible in one image plane may not be perceptible in another. A further disadvantage exists in these known diagnostic techniques, in that they are not readily applicable to all parts of the body's vascular system. For example, in the iliac segment of the human body, a high-risk region where stenoses leading to occlusions and critical ischaemia can occur, the anatomical region of interest is at least partially acoustically shielded by the abdominal organs. Ultrasonic methods are therefore very difficult to apply in this region.

From the above it is clear that there exists a need for a non-invasive technique for use in the prediction or the diagnosis of vascular disease which is simple, effective and cheap to employ such as to be appropriate for the screening of subjects.

The background to the present invention also includes the study of pulse volume recordings (PVRs). PVRs are used to give information about the dynamics of vascular pulsatile flow at sites in the human body and are generally studied as waveforms measured by means of a plethysmography cuff located at the site of interest, the waveform representing the pulsatile vascular pressure. PVRs are not intended to provide absolute blood pressures, but the shape of the waveform produced can give useful qualitative clinical information about the vascular system. Work involving the use of PVRs in vascular investigation is described, for example, in an article in The Journal of Vascular Surgery, Volume 13, Number 2, February 1991, pages 284 to 293, entitled "Impedance analysis to identify the at risk femorodistal graft", by M. G. Wyatt et al.

PVR analysis is available as a feature of a commercially available machine, the PVL-50 portable vascular laboratory available from Scimed Ltd in Bristol, United Kingdom. As well as a Doppler velocimeter and photoplethysmography system, the machine incorporates a pulse volume recorder, a single cuff for PVR monitoring, an integrated 128 point fast Fourier transform (FFT) analyser, and the software and hardware to gather, analyse, display and record clinical data. Amongst its functions, the PVL-50 incorporates the facility of pulse volume transfer function analysis. This involves the computation of a transfer function index, arrived at by integrating a transfer function curve, itself derived by dividing a Fourier transform of a recorded PVR from a first site, representing an output pulse, by that of a subsequent recorded PVR from a second site, representing an input pulse. No clinical significance of the transfer function index has hitherto been suggested, the function being included as a measurement curiosity. The PVL-50 is available accompanied by a user's manual explaining the function and use of the features available, but this gives no indication of any utility for this transfer function, and in any case only refers to the sequential measurement of PVRs at the two sites.

SUMMARY OF THE INVENTION

Recent work carried out using the PVL-50 between brachial and femoral sites has produced very surprising results and identified the significance of pulse volume transfer analysis in the assessment of vascular state, or more specifically, in the detection of vascular stenoses within the arterial system. At the root of the invention is the unexpected finding that the pulse volume transfer function index gives a highly useful, quick and simple indicator which can be evaluated to assess the presence and degree of sclerosis or stenosis of the blood vessel under investigation. A clinician may compare the index with a predetermined threshold value to give an immediate indication of whether the patient may be at risk or not. If a risk is identified, further validation methods can be applied, such as colour flow duplex ultra-sonography or biplanar angiography examination, to more clearly localise the stenosis. It has also been realised that other parameters of the transfer function also provide useful indicators as to the condition of a blood vessel segment.

This approach to vascular investigation is seen to provide a highly useful technique employing a relatively low-cost device for simple, reliable, repeatable, non-invasive indication of conditions likely to be associated with vascular sclerosis or stenoses in blood vessels within the human or animal body. If medical practice accepts preliminary diagnosis at a technician level then the apparatus and method of the present invention may be arranged to provide an indication which can be evaluated on a broadly calibrated basis.

According to a first aspect of the invention, then, a device suitable for use in assessing the state of blood vessels within the human or animal body is provided, comprising:

at least one blood pressure responsive device for application at different sites on the body;

pulse volume recorder means for coupling to the blood pressure responsive device or devices for producing waveform signals of pulsatile blood pressure at respective sites;

Fourier transform analysing means for analysing the waveform signals and obtaining Fourier transform spectra for respective sites;

transfer function computing means for determining a transfer function between respective sites; and transfer function analysing means for calculating a clinically significant parameter of the transfer function.

Preferably, the device has a store of at least one predetermined value against which the transfer function parameter can be compared to provide an assessment of vessel state.

In a preferred form, the transfer function analysing means is an integration means for integrating the transfer function.

The blood pressure responsive device may be a blood plethysmograph, such as an inflatable cuff of the type commonly used in blood pressure monitoring.

The device preferably comprises at least two blood pressure responsive devices for simultaneous application at respective sites. In the PVL-50 described above, pulse volume transfer analysis is possible, but a single cuff is provided and sequential cuffing of different sites is therefore necessary. The use of, say, a two-cuff device, affords considerable time saving and improves the reliability and reproducibility of the results obtained.

According to a second aspect of the invention, a method for assessing the state of blood vessels within the human or animal body is provided, comprising the steps of:

selecting a vessel segment for investigation;

obtaining pulse volume recordings (PVRs) representing pulsatile pressure at sites proximal and distal to the vessel segment;

performing Fourier transforms on the PVRs obtained at the two sites, to obtain a proximal transform spectrum ($FT_p$) and a distal transform spectrum ($FT_d$);

determining a transfer function (TF) where $TF[f]=FT_d[f]/FT_p[f]$, $TF[f]$, $FT_p[f]$ and $FT_d[f]$ representing the respective values at frequency f; and analysing TF to obtain a selected transfer function parameter of clinical significance.

Preferably, $FT_p$ and $FT_d$ are normalised with respect to amplitude before determination of TF.

The selected transfer function parameter may be compared with a predetermined value to provide an indication to a clinician as to whether or not the vessel segment may be at risk.

In a preferred form, TF is integrated to obtain, as the selected parameter, a transfer function index n.

The PVR representing pulsatile pressure at one of the sites may be obtained from a more accessible reference site.

The sites selected may be at a brachial position and a femoral position, representing respectively sites proximal and distal to the iliac arterial segment.

Preferably the PVRs are obtained simultaneously from the different sites.

In a form of the invention, a number of selected transfer function parameters giving information of clinical significance are obtained from analysis of TF.

BRIEF DESCRIPTION OF THE DRAWINGS

Further illustration of the invention is now given by way of example only with reference to the accompanying drawings, in which.

DETAILED DESCRIPTION OF THE INVENTION

Figure 1:
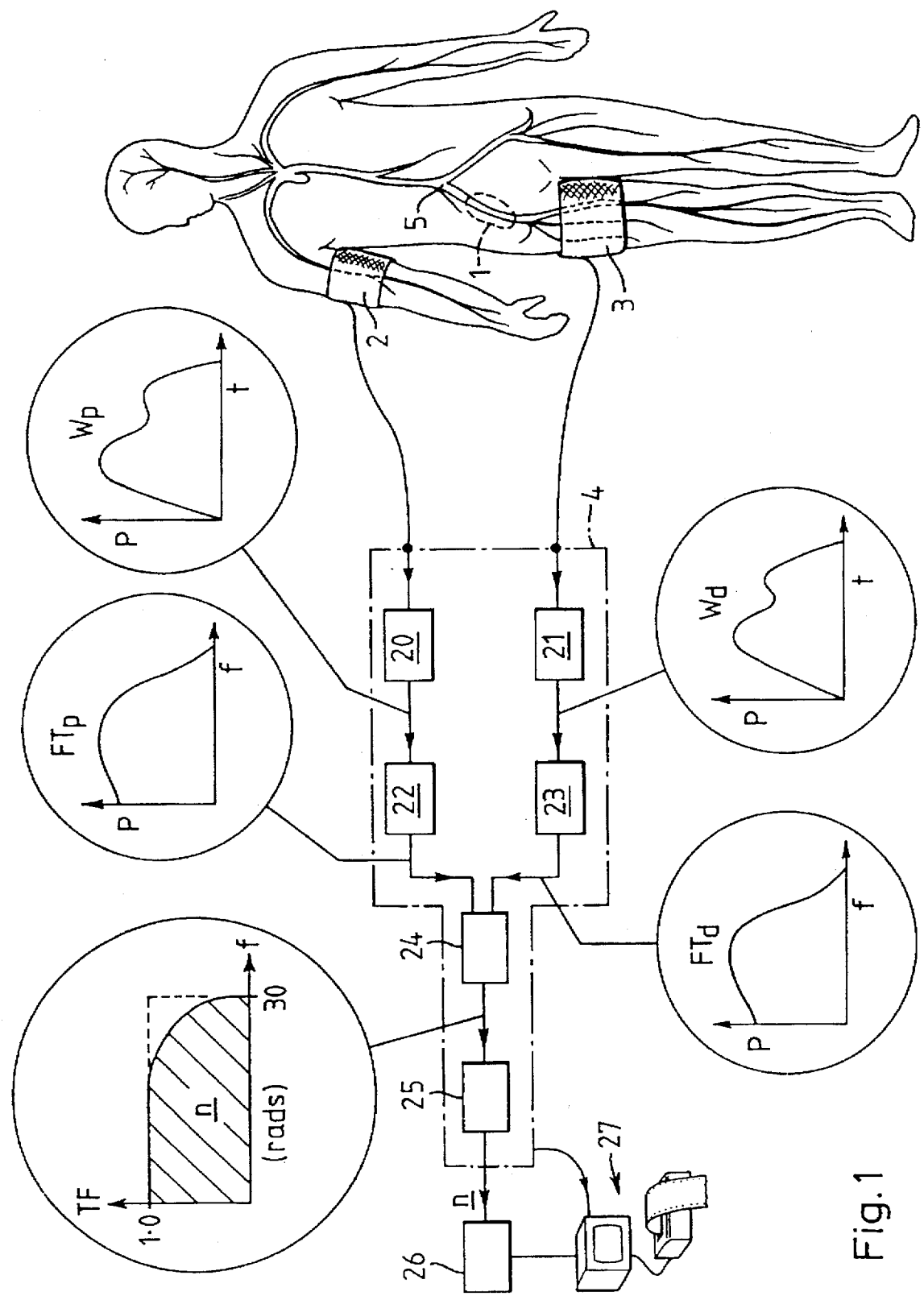
FIG. 1 shows a simplified representation of the human arterial system and illustrates the major components of the device of the present invention as applied to the human body.

In FIG. 1 the device of the invention is schematically represented applied to a test subject for the purposes of investigation of the iliac arterial segment 1. The device comprises two air plethysmography cuffs 2 (brachial) and 3 (femoral) which are placed around the top of the arm and the top of the thigh respectively, and a signal processor 4. Cuffs 2 and 3 are used to provide pulse volume recordings (PVRs) by means of conventional pulse volume recorders 20 and 21 respectively. As previously explained, PVRs indicate the waveform of the pulsatile arterial pressure at the relevant point in the vascular system.

The PVR recorded at the brachial cuff 2 approximates to the waveform which would be measured at the more inaccessible site of the proximal end of the iliac segment, at the post-abdominal aortal bifurcation point 5, say. The brachial site thus provides referred pressure from point 5. That measured at the femoral cuff 3 gives a distal PVR at a site downstream of the iliac segment, the two waveforms from the pulse volume recorders 20 and 21 thus effectively showing respectively input and output characteristics of the segment 1, as represented in the figure by the output waveforms of pressure against time $W_p$ (proximal) and $W_d$ (distal) from recorders 20 and 21 respectively. These recorders 20 and 21 also incorporate processors such that successive pulses can be sampled and accumulated to provide an averaged waveform for each cuff. The waveforms produced are then passed through conventional Fourier transform analysers 22 and 23 respectively and normalised to give proximal and distal Fourier transform spectra as shown in the figure by the curves $FT_p$ and $FT_d$ from the analysers 22 and 23 respectively. Fast Fourier transform analysers can also be used to perform this analysis. The spectra show normalised amplitude against frequency (radians) after normalisation of the vertical discrete Fourier axis.

The next step in the signal processing involves computation of the transfer function (TF). This is computed by dividing $FT_d$ by $FT_p$ along the frequency axis to produce an output transfer function curve TF as shown in the figure as the output from transfer function computing means 24. A TF value at a certain frequency is therefore calculated by the division of the $FT_d$ value by the $FT_p$ value at that frequency:

$TF[f]=FT_d[f]/FT_p[f]$, $TF[f]$, $FT_p[f]$ and $FT_d[f]$ representing the respective values at frequency f.

Since the FT plots have been normalised at the vertical Fourier axis, the TF value is therefore 1.0 at a frequency of zero. The horizontal frequency axis is limited to the first 30 radians so that outputs between successive tests are directly comparable.

The final step carried out by signal processor 4 is to directly calculate, by means of integrator 25, the area of the transfer function curve (the shaded area in the TF plot on the figure) to give a single transfer function index n, expressed as a fraction of the total area (Area/30). Clearly, if $FT_p$ and $FT_d$ are identical (up to 30 radians), the TF plot will be a horizontal line and the index will be 1.0, as shown by the dotted line on the TF plot in the figure.

In FIG. 1 an electronic store of at least one predetermined value is denoted by reference 26. Against this value or these values the transfer function index n can be automatically compared to provide an indication of the vessel state. The figure also shows at reference 27 a PC, screen and printer to provide display, printing and/or recording means for the data and results.

The components of the device required to implement the method described above are available pieces of standard equipment and will not be further described here. For example, amplifiers and analogue-digital converters used in such signal processing, waveform analysers and Fast Fourier Transform analysers, are readily available 'off-the-shelf' as hardware or software packages, and, as earlier explained, are available currently as a single piece of portable equipment in the form of the Scimed PVL-50. This includes a screen and a thermal printer, so that the traces (or spectra, in the case of the FT plots) can be presented (by display or printing) and examined by the clinician. Various parameters can be calculated and presented, including patient information and other data (such as date, time, operator details, etc.).

EVALUATION 1

The method described has been the subject of clinical evaluation to assess the potential for pulse volume transfer function analysis as a predictor of aorto-iliac disease. 31 aorto-iliac segments in patients with suspected iliac disease were investigated applying the above described brachial-femoral technique using the Scimed PVL-50. Each study took about 5 minutes and was virtually operator-independent, the operator only having to position the automatically-inflating cuffs and initiate the analysis. The results were compared with colour flow duplex ultrasonography and were followed by conventional angiography. The iliac arteries were classified as patent, stenotic (at least one haemodynamic stenosis on duplex or >50% on angiography) or occluded. The results are set out below.

| [mean/standard deviation] | Patent (18 patients) | Stenotic (8 patients) | Occluded (5 patients) |
|---|---|---|---|
| n(pulse volume transfer function index) | 1.05/0.13 | 0.72/0.11 | 0.67/0.08 |

The results show a significant and surprising correlation between arterial condition and transfer function index, and indicate that the analysis can provide to a clinician a highly useful indicator/predictor of stenotic/occluded arteries. A patient whose n index is less than 0.8, for example, may be at risk, and such a result would therefore be followed up by closer investigation, e.g. by conventional biplanar angiography. The effect is detectable considerably in advance of significant haemodynamic deterioration over the segment. It is thought by the inventors of this invention that in some way the stenosed segment behaves rather like a lowpass filter. The transfer function represents the frequency response of the relevant segment, and the progressive reduction in transfer function index arises as the higher frequencies are increasingly attenuated as the vessel progressively narrows. In healthy subjects the index n is generally greater than 1, because of various haemodynamic factors associated with elastic vessels.

EVALUATION 2

A second study was undertaken, investigating 82 aorto-iliac segments in 42 patients with suspected iliac arterial disease. The pulse volume transfer function analysis results were again compared with colour flow duplex ultrasonography and conventional angiography to classify the degree of claudication of each segment under investigation. A control group of 42 aorto-iliac segments in 21 volunteers with no vascular disease were assessed by pulse volume transfer function analysis alone.

Figure 2:
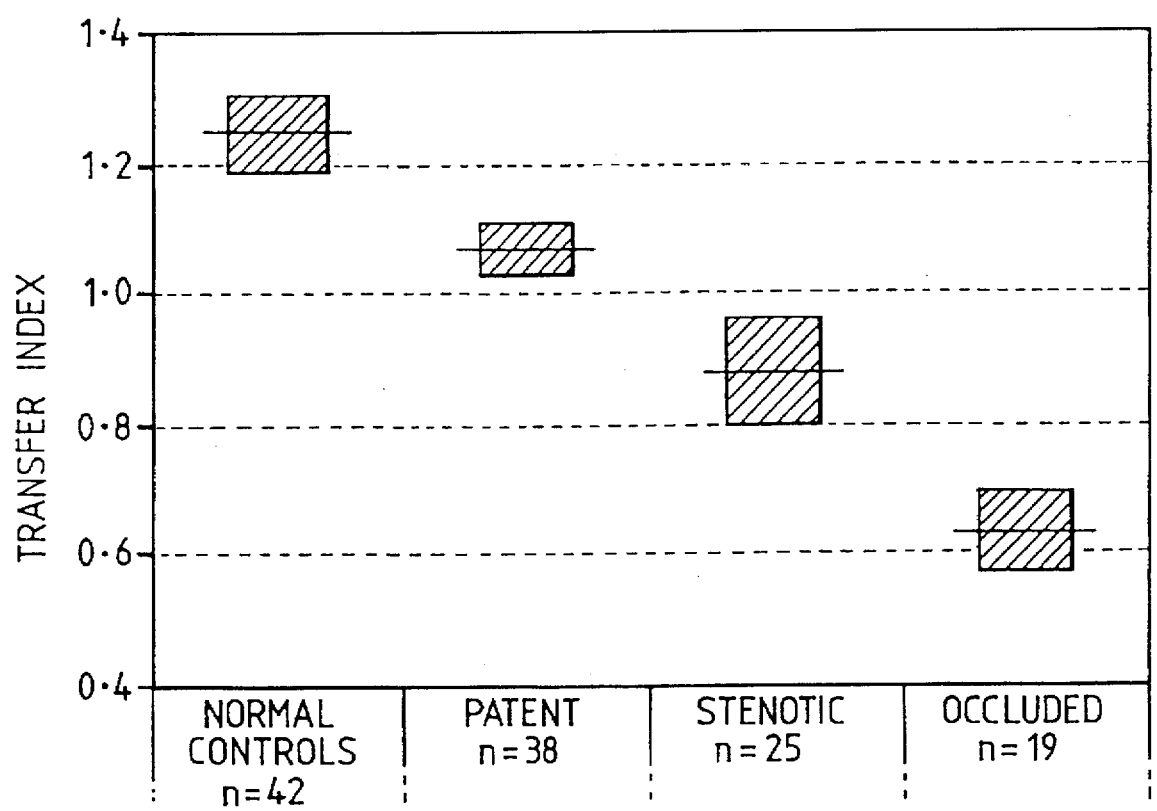
FIG. 2 illustrates a set of results from clinical evaluation trials in respect of the method of the present invention.

The results are graphically presented in FIG. 2, which shows the 95% confidence limits for the results for the vascular segments investigated falling into each of the 4 categories. Once again, these results show clearly that this method of assessment can be used to provide an indication of which vessels may be at risk.

Furthermore, research into the transfer function has shown that other characteristics of the curve, other than the index n, can also give clinically valuable quantitative information, of use in evaluating the presence and degree of vascular stenosis or sclerosis.

For example, curve fitting techniques to mathematically define the transfer function can give parameters for the curve which can provide very sensitive differentiation between states of vessel segments tested. The device can be arranged to compare one or more of such parameters with predetermined values to provide an indication to a clinician as to whether or not a patient is to be considered 'at risk'. Such analysis techniques can be readily automated, of course, by use of the appropriately programmed PC 27 in FIG. 1.

As explained earlier, the invention envisages the simultaneous use of two cuffs, which represents a considerable advance over the sequential use of a single cuff, as available currently on the PVL-50. With a single cuff it is necessary sequentially to cuff and wake recordings at the proximal and distal sites, store the PVRs produced, and then initiate the analysis. Simultaneous recording by two cuffs at the two sites thus affords a valuable time saving. Moreover, the PVRs taken sequentially are less likely to be directly comparable, even if averaged over a certain train of pulses, than PVRs taken of the same pulse or pulses. The use of simultaneous recording therefore reduces possible error in the resulting pulse volume transfer analysis. Only one Fourier transform analyser is required for this, as the PVRs representing the two sites can be multiplexed to the single analyser. Additionally, this two cuff arrangement allows the provision of information regarding the pulse time delay between sites, which can also be of use in assessing the condition of the intermediate vessel segment.

The invention has been illustrated with reference to brachial-femoral transfer function analysis in respect of the iliac segment. Clearly, though, it may be applied to any other sites and/or in respect of other vessel segments where a PVR can be obtained. A multiplicity of cuffs can be employed, each cuff placed at a different position on the limbs, enabling rapid identification and location of a stenosis. Moreover, alternative blood plethysmographic methods for pulse volume recording can be employed. Photoplethysmographic probes can be used, applicable, for example, to the digits. Tonometric probes can also be used, applicable, for example, to the eye. Stroke prediction may be accomplished using a tonometer on the eye in combination with a brachial cuff to detect stenosis in the carotid artery.

The present invention may be used not only in the prediction/indication of vascular disease, especially in its early stages, but also in pre- and post-operative monitoring, for example in the case of balloon/patch angioplasty or vascular graft operations.

Although described in relation to a non-invasive technique using plethysmographic methods, the present invention also has application to invasive investigation, where more direct methods of pressure monitoring can be used. In particular, a catheter provided with mutually displaced pressure transducers may be introduced into the lumen of a vessel under investigation and the transfer function analysis carded out on the waveforms corresponding to the positions of the two transducers. Applications of this include the investigation of cardiac lesions, and the monitoring of arterial dilatation operations. In the latter example, the pressure transducers can be simply built into a dilatation catheter and the analysis can be carried out pre- and post-dilatation to determine the efficacy of the operation.

The embodiment of the invention described above and illustrated in the accompanying figure is given by way of example only and it should be understood that this in no way limits the scope of the invention.

Although specifically developed for arterial conditions clearly the techniques above are equally applicable to various conditions and could be applied with appropriate modification appreciable to those skilled in the art to, say, the venous system.

We claim:

1. A device suitable for use in an assessment of blood vessels within a human or animal body, comprising:
   at least one blood pressure responsive device for application at different sites on the body;
   pulse volume recorder means for coupling to the blood pressure responsive device or devices for producing waveform signals of pulsatile blood pressure at respective sites;
   Fourier transform analyzing means for analyzing the waveform signals and obtaining Fourier transform spectra for respective sites;
   transfer function computing means for determining a transfer function between respective sites;
   transfer function analyzing means for directly extracting a clinically significant parameter of the transfer function;
   a store of at least one predetermined value against which the transfer function parameter is compared; and
   means for indicating a result of said comparison, indicative of the state of the blood vessel between the respective sites.

2. A device suitable for use in an assessment of blood vessels within a human or animal body, comprising:
   at least one blood pressure responsive device for application at different sites on the body;
   pulse volume recorder means for coupling to the blood pressure responsive device or devices for producing waveform signals of pulsatile blood pressure at respective sites;
   Fourier transform analyzing means for analyzing the waveform signals and obtaining Fourier transform spectra for respective sites;
   transfer function computing means for determining a transfer function between respective sites;
   transfer function analyzing means for directly extracting a clinically significant parameter of the transfer function;
   a store of at least one predetermined value against which the transfer function parameter is compared; and
   means for indicating a result of said comparison,
   wherein said transfer function analyzing means is an integration means, the parameter being the integral of the transfer function.

3. A device according to claim 1 or claim 2, including as a blood pressure responsive device a blood plethysmograph of inflatable cuff type.

4. A device according to claim 2, comprising at least two blood pressure responsive devices for simultaneous application at respective sites.

5. A device according to claim 2, including at least one selected from the group consisting of a display, printing and recording means.

6. A method for an assessment of blood vessels within a human or animal body comprising the steps of:
   selecting a vessel segment for investigation;
   obtaining pulse volume recordings (PVRs) representing pulsatile pressure at sites proximal and distal to the vessel segment;
   performing Fourier transforms on the PVRs obtained at said proximal and distal sites, to obtain a proximal transform spectrum ($FT_p$) and a distal transform spectrum ($FT_d$);
   determining a transfer function (TF) where
   $TF[f]=FT_d[f]/FT_p[f]$,
   $TF[f]$, $FT_p[f]$ and $FT_d[f]$ representing the respective values at frequency f;
   extracting from TF a selected transfer function parameter;
   comparing the selected transfer function parameter with a predetermined value; and
   indicating a result of said comparison as representative of whether the vessel segment may be at risk.

7. A method according to claim 6, including the step of normalising $FT_p$ and $FT_d$ with respect to amplitude before determination of TF.

8. A method according to claim 6 or claim 7, wherein TF is integrated to obtain, as the selected parameter, a transfer function index n.

9. A method according to claim 6, wherein the PVR representing pulsatile pressure at one of the sites is obtained from an alternative reference site.

10. A method according to claim 9, wherein the sites selected are at a brachial position and a femoral position, representing respectively sites proximal and distal to an iliac arterial segment.

11. A method according to claim 6, wherein the PVRs are obtained simultaneously from said proximal and distal sites.

12. A method according to claim 6, wherein a number of selected transfer function parameters giving information of clinical significance are obtained from analyzing TF.

* * * * *